(12) United States Patent
Berghaus et al.

(10) Patent No.: US 12,313,613 B2
(45) Date of Patent: May 27, 2025

(54) METHOD OF TESTING CRYSTALLINITY IN AMORPHOUS PHARMACEUTICAL COMPOSITIONS

(71) Applicant: ColVisTec AG, Berlin (DE)

(72) Inventors: Andreas Berghaus, Berlin (DE); Angela Spangenberg, Georgetown, TX (US)

(73) Assignee: COLVISTEC AG, Berlin (DE)

( * ) Notice: Subject to any disclaimer, the term of this patent is extended or adjusted under 35 U.S.C. 154(b) by 879 days.

(21) Appl. No.: 17/426,451

(22) PCT Filed: Jan. 29, 2020

(86) PCT No.: PCT/EP2020/052175
§ 371 (c)(1),
(2) Date: Jul. 28, 2021

(87) PCT Pub. No.: WO2020/160980
PCT Pub. Date: Aug. 13, 2020

(65) Prior Publication Data
US 2022/0120726 A1 Apr. 21, 2022

(30) Foreign Application Priority Data

Feb. 5, 2019 (GB) ...................................... 1901579

(51) Int. Cl.
*G01N 33/15* (2006.01)
*G01N 21/31* (2006.01)
(Continued)

(52) U.S. Cl.
CPC ......... *G01N 33/15* (2013.01); *G01N 21/4738* (2013.01); *G01N 21/55* (2013.01);
(Continued)

(58) Field of Classification Search
CPC ........ G01N 21/31; G01N 21/55; G01N 21/59; G01N 21/4738; G01N 33/15;
(Continued)

(56) References Cited

U.S. PATENT DOCUMENTS

2003/0123057 A1 7/2003 Lemmo et al.
2003/0129753 A1 7/2003 Lee
(Continued)

FOREIGN PATENT DOCUMENTS

CA 2828363 A1 3/2015
CN 101460831 A 6/2009
(Continued)

OTHER PUBLICATIONS

International Search Report and Written Opinion issued for International Application No. PCT/EP2020052175 on Jun. 2, 2020.
(Continued)

*Primary Examiner* — John H Le
(74) *Attorney, Agent, or Firm* — Klarquist Sparkman, LLP

(57) ABSTRACT

Methods of testing pharmaceutical compositions for the presence or absence of active pharmaceutical ingredient (API) crystallinity in an amorphous solid dispersion or solid-state solution using UV/vis spectrometry is provided. Testing may be performed standalone or during manufacturing of a pharmaceutical composition. A predictive model provides for quantitative analysis of the amount of crystalline API based on UV/vis data of corresponding reference samples. Also provided is an apparatus for manufacturing a pharmaceutical composition.

16 Claims, 12 Drawing Sheets

(51) Int. Cl.
  *G01N 21/3563*  (2014.01)
  *G01N 21/47*  (2006.01)
  *G01N 21/55*  (2014.01)
  *G01N 21/59*  (2006.01)

(52) U.S. Cl.
  CPC ..... *G01N 21/59* (2013.01); *G01N 2021/3155* (2013.01); *G01N 2021/3572* (2013.01); *G01N 2021/558* (2013.01); *G01N 2201/129* (2013.01)

(58) Field of Classification Search
  CPC ....... G01N 2021/129; G01N 2021/558; G01N 2021/3155; G01N 2021/3572
  USPC .......................................................... 702/28
  See application file for complete search history.

(56) References Cited

U.S. PATENT DOCUMENTS

| | | | |
|---|---|---|---|
| 2008/0165354 A1 | 7/2008 | Rantanen et al. | |
| 2013/0187050 A1 | 7/2013 | Takebe et al. | |
| 2015/0011525 A1* | 1/2015 | Bi | A61K 9/1635 264/141 |

FOREIGN PATENT DOCUMENTS

| | | |
|---|---|---|
| CN | 103760124 A | 4/2014 |
| GB | 2237303 A | 5/1991 |
| KR | 20170075090 A | 7/2017 |
| WO | WO2004061433 A1 | 7/2004 |
| WO | WO 2004/071486 A1 | 8/2004 |
| WO | WO 2007/113566 A2 | 10/2007 |
| WO | WO2008/073424 A2 | 6/2008 |
| WO | WO2013040187 A1 | 3/2013 |
| WO | WO 2016/118633 | 7/2016 |

OTHER PUBLICATIONS

Regmi et al., "Insight into phosphate doped BiVO4 heterostructure for multifunctional photocatalytic performances: A combined experimental and DFT study," *Applied Surface Science*, vol. 466, pp. 787-800, Oct. 9, 2018.

Schlindwein et al., "In-line UV-Vis spectroscopy as a fast-working process analytical technology (PAT) during early phase product development using hot melt extrusion (HME)," *Pharmaceutics*, 10(4): 1-25, Sep. 23, 2018.

Search Report issued for GB Application No. 1901579.1 on Nov. 29, 2019.

Thiel et al., "Manufacturing amorphous solid dispersions with a tailored amount of crystallized API for biopharmaceutical testing," *Mol. Pharmaceutics*, 15(5): 1870-1877, Apr. 12, 2018.

Ueda et al., "Raman mapping for kinetic analysis of crystallization of amorphous drug based on distributional images," *International Journal of Pharmaceutics*, 462(1-2): 115-122, Dec. 22, 2013.

Wesholowski et al., "Inline UV/Vis spectroscopy as PAT tool for hot-melt extrusion," *Drug Delivery and Translational Research*, vol. 8, pp. 1595-1603, Jan. 11, 2018.

Anderson et al., "Determination of the onset of crystallization of $N^1$-2-(thiazolyl) sulfanilamide (sulfathiazole) by UV-Vis and calorimetry using an automated reaction platform; subsequent characterization of polymorphic forms using dispersive Raman spectroscopy," *Spectrochimica Acta Part A*, 57 (2001) 1793-1808.

Chen et al., "Quality Detection of Metronidazole Based on Near Infrared Spectroscopic Analysis," Chinese Journal of Pharmaceutical Analysis, 2003, pp. 89-91; *Document unavailable*.

Examination Report for India Patent Application No. 202147036712, dated Sep. 13, 2023, 6 pages.

Feng et al., "High-throughput crystallization in pharmaceutical research and development," Acta Pharmaceutica Sinica, (2005), pp. 481-485.

Major et al., "Perichromism: A Novel, Rapid, Spectroscopic Technique to Distinguish Between Amorphous and Crystalline Material," *Applied Spectroscopy*, vol. 65(12), 2011, 1357-1362.

Office Action for Chinese Patent Application No. 202080012418.8, dated Jan. 31, 2024, 15 pages (English Translation).

Schlindwein et al., "In-Line UV-Vis Spectroscopy as a Fast-Working Process Analytical Technology (PAT) during Early Phase Product Development Using Hot Melt Extrusion (HME)," *Pharmaceutics*, 2018, 10, 166, doi:10.3390/pyarmaceutics 10040166.

Search Report for Chinese Patent Application No. 2020800124188, dated Jan. 25, 2024, 4 pages (English Translation).

Ueda et al., "Raman mapping for kinetic analysis of crystallization of amorphous drug based on distributional images," *International Journal of Pharmaceutics*, 462 (2014) 115-112.

* cited by examiner

METHOD OF TESTING CRYSTALLINITY IN AMORPHOUS PHARMACEUTICAL COMPOSITIONS

CROSS REFERENCE TO RELATED APPLICATIONS

This application is the § 371 U.S. National Stage of International Application No. PCT/EP2020/052175, filed Jan. 29, 2020, which was published in English under PCT Article 21 (2), which in turn claims the benefit of and priority from GB1901579.1, filed 5 Feb. 2019, the contents and elements of which are herein incorporated by reference for all purposes.

FIELD OF THE DISCLOSURE

The present invention relates to the presence of crystallinity in otherwise amorphous pharmaceutical compositions. Among other things, it relates to a method of detecting, and optionally quantifying, the crystallinity of otherwise amorphous pharmaceutical compositions.

BACKGROUND

Products manufactured in the pharmaceutical industry are required to meet very stringent quality standards. This is because the adverse effects of substandard pharmaceutical products pose a widespread threat to public safety. Previously, there was a higher incidence of substandard pharmaceutical compositions reaching the market. In an attempt to decrease the incidence of substandard pharmaceutical compositions reaching the market the pharmaceutical industry has seen extensive and increasing regulatory demands.

Pharmaceutical companies often have dedicated quality control departments to ensure their pharmaceutical compositions meet the relevant regulatory standards. Meeting regulatory standards carries a large financial burden due to the time, personnel and equipment that is needed. It is desirable to decrease the amount of time and money required to meet regulatory standards without compromising quality.

Process analytical technology (PAT) is used to effectively design and control pharmaceutical manufacturing processes by monitoring specific quality indicators and parameters. The pharmaceutical manufacturing industry is evolving and there is regulatory pressure to switch from batch-based manufacture to continuous manufacture. PAT has particular relevance for emerging continuous manufacturing methods.

There are a number of factors that are assessed in the quality control of pharmaceutical compositions. One of those factors is the physical form. Active pharmaceutical ingredients (APIs) can exist in a variety of distinct solid forms, including polymorphs, solvates, hydrates, salts, co-crystals and amorphous solids. Each form displays unique physicochemical properties that can greatly influence the bioavailability, manufacturability, purification, stability and other characteristics.

Crystallinity, and in particular crystal polymorphism, can greatly affect the solubility, bioavailability and stability of many APIs. By co-formulating small molecule APIs with water-soluble polymers, significant increases in drug absorption kinetics and overall bioavailability are observed.

Hence, there is significant interest in producing "amorphous solid dispersions" of API, where a crystalline material is rendered amorphous by virtue of being "dissolved", i.e. molecularly dispersed, and no longer crystalline, by incorporation into a molten polymer phase.

Efficient mixing and sufficient mechanical energy are required to produce an adequately dispersed amorphous product. However, it is not straightforward to determine the extent of dissolution/dispersion, particularly in an on-line setting.

Typically, to determine the level of residual crystalline material present in a solid sample, it is first necessary to mill the solid to a homogeneous powder, and then analyse in a powder X-ray diffractometer. Powder XRD is not a rapid process, is performed off-line and usually takes between 15 mins to 1 hour to achieve a result.

It is also possible to use Raman spectroscopy to measure levels of crystallinity in such solid samples, see e.g. Thiel et al., Manufacturing Amorphous Solid Dispersions with a Tailored Amount of Crystallized API for Biopharmaceutical Testing, *Mol. Pharmaceutics,* 2018, 15 (5), pp 1870-1877 reporting studies on crystal growth in fenofibrate tablets over time. However, Raman spectroscopy is difficult to use in an in-line manufacturing setting, due to complexities associated with laser light, laser safety and the generally long integration times required to obtain useful spectra.

In view of the above there is a need for improved methods and apparatuses to monitor and manufacture high quality amorphous pharmaceutical compositions.

WO 2016/118633 A1 describes quantification and preparation of pharmaceutical grade cantharidin. US 2008/0165354 A1 describes a method and apparatus for dissolving solid matter in liquid.

The use of in-line UV/vis spectroscopy as a fast-working process analytical technology (PAT) during early phase product development using hot melt extrusion is known, see *Pharmaceutics* 2018, 10, 166.

The present disclosure has been devised in the light of the above considerations.

SUMMARY OF THE DISCLOSURE

In a first aspect of the invention, there is provided a method of generating a predictive model for determining the amount of crystallinity of an API in an amorphous solid dispersion or solid-state solution comprising the steps of; (i) subjecting a plurality of reference samples of dispersions or solutions spanning a range of API crystallinity amounts to UV/vis spectroscopy, (ii) measuring a reflectance and/or transmission spectrum of each reference sample, and (iii) processing the spectra gathered in step (ii) to generate a predictive crystallinity model.

References herein to "dispersions" and "solutions" mean "amorphous solid dispersions" and "solid-state solutions" respectively.

By generating a predictive model in this way, it is possible to determine the quantitative amount of crystallinity of an API in a dispersion or solution, such as in the method provided in the first aspect of the invention.

In some cases, the number of reference samples is 5 or more.

In some instances, the spectra are pre-processed before step (iii) to normalise and/or smooth the spectra In some cases, the spectra of the reference samples are processed to derive a feature that correlates with crystallinity across at least a portion of said range of crystallinity.

In some instances, said feature comprises: at least a first principle component derived from principle components analysis (PCA) of the spectra, optionally wherein the variance of said first principle component by crystallinity is substantially linear across the range of crystallinity of said plurality of dispersions or solutions; or a lightness value L* of CIELAB colour space derived from the spectra.

In a second aspect of the invention, there is provided a method of testing a pharmaceutical composition comprising an API in an amorphous solid dispersion or solid-state solution for crystallinity of the API comprising the steps of; (i) subjecting the dispersion or solution to UV/vis spectroscopy, (ii) measuring a reflectance and/or transmittance spectrum, and (iii) determining the presence or absence of crystallinity of the API by comparing measured reflectance and/or transmittance spectrum to that expected for a completely amorphous sample.

The transmission/absorbance and reflectance of the amorphous solid dispersion or solid-state solution has been found to correlate to the crystallinity of the API. As applied here, UV/vis spectroscopy does not rely on the transition of electrons between orbitals. Without wishing to be bound by theory, the present invention relies on the scattering of light by API crystals present in the otherwise amorphous pharmaceutical composition. An advantage is fast and inexpensive detection of API crystallinity of otherwise amorphous dispersions or solutions.

In some cases, when crystalline API is found to be present, there is a step of determining the amount crystallinity in the dispersion or solution by comparing the observed spectrum to the predictive model, such as a standard curve.

In some instances, the predictive model is according to the first aspect of the invention.

In some cases, comparing the observed spectrum to the predictive model comprises processing the observed spectrum in the same way as the spectra of said plurality of reference samples.

In some instances, the amount of crystallinity in the dispersion or solution is measured at 50 wt % and below, such as 25 wt % and below or 20 wt % and below or 15 wt % and below.

In some cases, the amount of crystallinity in the dispersion or solution is measured at 1 wt % and above, such as 2 wt % and above or 3 wt % and above or 5 wt % and above.

In a third aspect of the invention, there is provided a method of manufacturing a pharmaceutical composition comprising the steps of; (i) forming an API into an amorphous solid dispersion or solid state solution, (ii) testing the dispersion or solution for crystallinity of the API one or more times according to the second aspect of the invention, and (iii) where the dispersion or solution has an amount of crystallinity within an acceptable range, processing the composition into a finished pharmaceutical product.

By testing the dispersion or solution for crystallinity of the API one or more times, an advantage is that a high quality pharmaceutical composition meeting the required regulatory standards may be manufactured with improved reliability and consistency. There is decreased waste of time, money and resources because efficiency of manufacturing is increased.

In some cases, the forming of the API into a dispersion or solution is performed by extrusion, ball-milling or spray drying; and/or the testing of the dispersion or solution for the presence or absence of crystallinity one or more times is performed in-line.

In some instances, the forming is performed by extrusion and the testing is performed at one or more of the point of API input, upstream of the point of extrusion and at the point of extrusion.

In some cases, the forming is performed by ball-milling in a ball mill having one or more transparent points wherein the testing is performed through the one or more transparent points substantially perpendicular to the axis of motion.

In some instances, the forming is performed by spray drying and the testing is performed at one or more of the point of API input, at the point of atomisation in a drying chamber or at the point of settling after atomisation.

In some cases, the acceptable range for crystallinity is 1 wt % or less. The acceptable range for crystallinity may also be 0.25 wt % or less, 0.5 wt % or less, 2 wt % or less or 3 wt % or less.

In some instances, the amount of API input to the screw extruder, ball mill or spray drier is automatically adjusted, when required, to ensure crystallinity is within the acceptable range.

In some cases, the speed of the screw extruder, ball mill or spray drier is automatically adjusted, when required, to ensure crystallinity is within the acceptable range.

In some instances, the temperature of the extruder barrel or spray drier is automatically adjusted, when required, to ensure crystallinity is within the acceptable range.

In some cases, UV/vis reflectance and/or transmittance are measured continuously, such as 7 times per second, 5 times per second or 2 times per second.

In some instances, the reflectance and/or transmittance spectrum is measured at wavelengths of 210 to 800 nm, such as 300 to 700 nm, preferably 315 nm to 400 nm (UVA).

In some cases, only the reflectance spectrum is measured.

In some instances, only the transmission spectrum is measured.

In some cases, the particle size of the dispersion or solution is measured prior to being subjected to UV/vis spectroscopy. Known methods of sizing the dispersion or solution include sieve analysis, direct imaging and laser diffraction. In the present disclosure, a Mastersizer (Malvern Instruments) laser diffraction device was used.

In some instances, the dispersion or solution is sized to match the size of one or more reference samples of known crystallinity, wherein the reference samples match the API and carrier of the dispersion or solution.

In some cases, the API is a compound of 2000 g/mol or less molecular weight, such as small molecule drugs of 1000 g/mol or less. In some cases, the API is a compound of 100 g/mol or more molecular weight, such as 200 g/mol or more.

In some instances, the API is at least 95% pure prior to being incorporated into said dispersion or solution, such as at least 97% pure or at least 99% pure.

In some cases, the API comprises 5 wt % or less water. Preferably, the API comprises 3 wt % or less water, such as 1 wt % or less water.

In some instances, the API is a non-nucleoside reverse transcriptase inhibitor (NNRTI), preferably etravirine (ETR), or is a non-steroidal anti-inflammatory drug (NSAID), preferably piroxicam (PRX). The API may be an orally administrable drug of any class that has at least one crystalline form.

In some cases, the carrier of the dispersion or solution comprises an amorphous polymer. Naturally, an amorphous solid dispersion or solid-state solution comprises a carrier in which the other components are dispersed or "dissolved".

In some instances, the amorphous polymer is one or more of a cellulose polymer, a vinyl polymer, a polymethacrylate polymer and a polyalkylene glycol polymer.

In some cases, the amorphous polymer is one or more of ethyl cellulose, hydroxyethyl cellulose, hydroxypropyl cellulose, hydroxypropyl methylcellulose (HPMC), HPMC acetate succinate (HPMCAS); polyvinyl acetate phthalate; polymethacrylates; polyalkylene glycols such as polyethylene glycol (PEG), copolymers of PEG, polypropylene glycol (PPG), poloxamers (triblock polymers with a central hydrophobic PPG block flanked by two hydrophilic PEG blocks), soluplus (a PEG-polyvinyl acetate-polyvinyl caprolactam graft copolymer (PVAc-PVCap-PEG)); polyvinylpyrrolidone (povidone), copovidone, vinylpyrrolidone-vinyl acetate copolymers and a linear random copolymer (e.g. 60:40) of N-vinyl-2-pyrrolidone and vinyl acetate.

In some instances, the amorphous polymer is one or more of Kollidon® VA 64, Soluplus®, Kollidon® 12 PF, Kollidon® 17 PF, Kollidon® 30, Kollidon® 90 F, Kollidon® SR, Kollicoat® MAE 100P, Kollicoat® IR, Kollicoat® Protect, Kolliphor® P407, Kolliphor® P407 micro, Kolliphor® P188, Kolliphor® P188 micro, Kolliphor® PEG grades, Kolliphor® RH 40 and Kolliphor® TPGS as provided by BASF.

In some cases, the carrier of the dispersion or solution comprises 5 wt % or less water. Preferably, the dispersion or solution comprises 3 wt % or less water, such as 1 wt % or less water.

In some instances, the dispersion or solution comprises 5 wt % or less water. Preferably, the dispersion or solution comprises 3 wt % or less water, such as 1 wt % or less water.

In a fourth aspect of the invention, there is provided an apparatus for forming a pharmaceutical composition as an amorphous solid dispersion or solid-state solution comprising a quality control system for testing the amount of crystallinity of an API in the composition by means of one or more UV/vis spectrometers configured to measure reflectance and/or transmittance intensity.

By having such an apparatus, the amount of crystalline API in an amorphous solid dispersion may be determined rapidly and inexpensively without requiring a separate apparatus. Thus, quality control is integral to the apparatus, rather than a separate off-line entity.

In some instances, the apparatus comprises a screw extruder, a ball mill or a spray drier, wherein the or each UV/vis spectrometer is positioned at an in-line measurement point to measure reflectance and/or transmittance of the dispersion or solution. By positioning the UV/vis spectrometer in-line, the results of the reflectance and/or transmittance measurements may be used immediately to modify parameters of the extrusion as necessary.

In some cases, the apparatus comprises a screw extruder and the or at least one of the UV/vis spectrometers is configured to measure reflectance and/or intensity at one or more of the point of API input, upstream of the point of extrusion and the point of extrusion.

In some instances, the apparatus comprises a ball mill having one or more transparent points wherein the or at least one of the UV/vis spectrometers is configured to measure reflectance and/or transmittance through the one or more transparent points and substantially perpendicular to the axis of motion.

In some cases, the apparatus comprises a spray drier and the or at least one of the UV/vis spectrometers is configured to measure reflectance and/or transmittance at one or more of the point of API input, the point of atomisation in a drying chamber and the point of settling after atomisation.

In some instances, the or each UV/vis spectrometer is photonically connected to a probe at the or each measurement point by optical fibre. The tip of each probe may comprise a sapphire window. Preferably, each optical fibre is 20 meters or shorter in length. The UV/vis spectrometer may comprise a Xenon flash lamp for illumination via the optical fibres.

In a reflection polymer melt probe (RPMP), each optical fibre may have six circumferentially positioned glass fibres for illumination and a centrally positioned glass fibre for reflectance. The light travels to the measurement point by the circumferentially positioned glass fibres and returns via the centrally positioned glass fibre for reflectance.

In a transmission polymer melt probe (TPMP), there are two separate units that are placed at a distance across the path of the solution or dispersion. One unit provides illumination whereas the other unit collects light transmitted through the solution or dispersion across the path. The distance between the two units can be varied to optimise measurement of cases dispersion or solution in the pathway.

In some instances, the apparatus is configured to automatically adjust the amount of API input to the screw extruder, ball mill or spray drier, when required, in response to the in-line measurements of the or each UV/vis spectrometer.

In some instances, the apparatus is configured to automatically adjust the speed of the screw extruder, ball mill or spray drier, when required, in response to the in-line measurements of the or each UV/vis spectrometer.

In some cases, the apparatus is configured to automatically adjust the temperature of the screw extruder, ball mill or spray drier, when required, in response to the in-line measurements of the or each UV/vis spectrometer.

In some instances the spectrometer is configured to measure reflectance and/or transmittance intensity over the region of 210 to 800 nm, such as 300 to 700 nm or 315 nm to 400 nm (UVA).

In some cases, the or each UV/vis spectrometer is configured to measure reflectance and/or transmittance continuously, such as at least 1 time per second, at least 2 times per second, at least 5 times per second or at least 7 times per second.

In some instances, the apparatus is for use with the method according to the third aspect of the invention.

SUMMARY OF THE FIGURES

So that the invention may be understood, and so that further aspects and features thereof may be appreciated, embodiments illustrating the principles of the invention will now be discussed in further detail with reference to the accompanying figures, in which.

DETAILED DESCRIPTION

Figure 1:
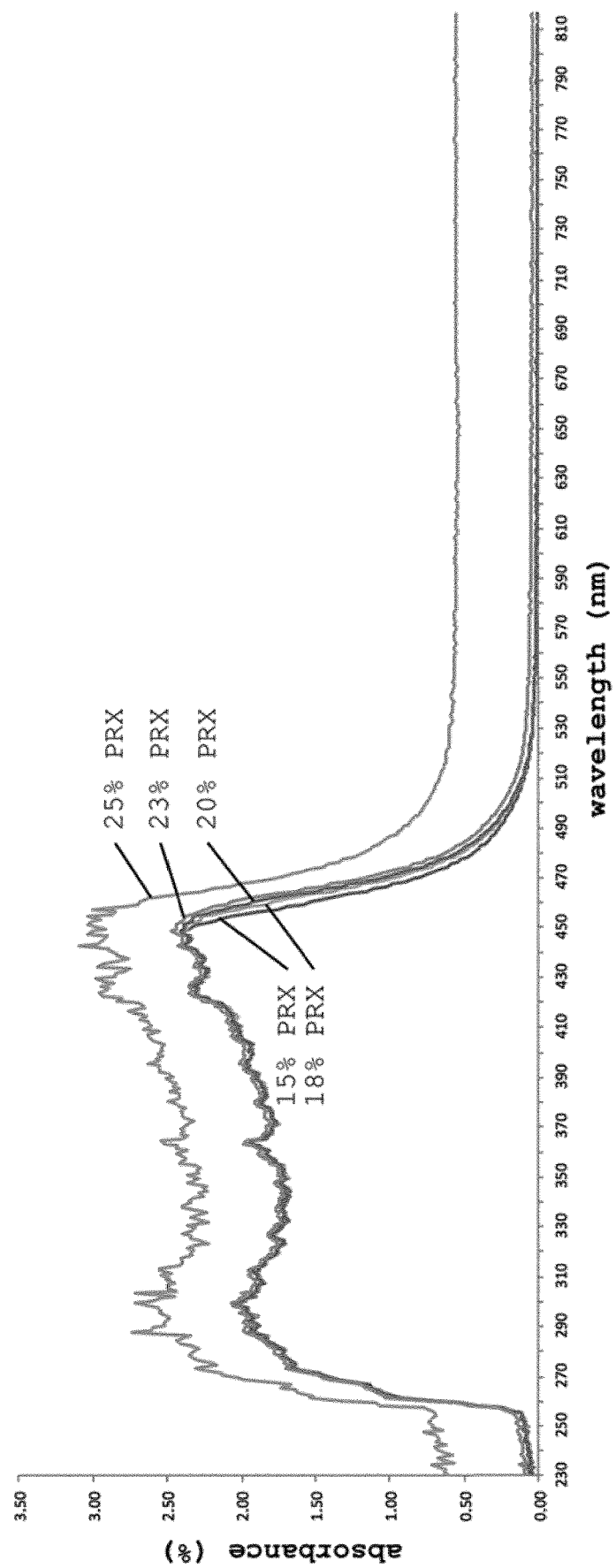
FIG. 1 shows five UV/vis transmission spectra of 15, 18, 20, 23 and 25 wt % PRX samples at 230 to 810 nm. An overall increase in absorbance is seen with increasing amounts of PRX with a particularly large increase in overall absorbance is observed between 23% and 25% PRX.

The features disclosed in the foregoing description, or in the following claims, or in the accompanying drawings, expressed in their specific forms or in terms of a means for performing the disclosed function, or a method or process for obtaining the disclosed results, as appropriate, may, separately, or in any combination of such features, be utilised for realising the invention in diverse forms thereof.

While the invention has been described in conjunction with the exemplary embodiments described above, many equivalent modifications and variations will be apparent to those skilled in the art when given this disclosure. Accordingly, the exemplary embodiments of the invention set forth above are considered to be illustrative and not limiting. Various changes to the described embodiments may be made without departing from the scope of the invention.

For the avoidance of any doubt, any theoretical explanations provided herein are provided for the purposes of improving the understanding of a reader. The inventors do not wish to be bound by any of these theoretical explanations.

Any section headings used herein are for organizational purposes only and are not to be construed as limiting the subject matter described.

Throughout this specification, including the claims which follow, unless the context requires otherwise, the words "have", "comprise", and "include", and variations such as "having", "comprises", "comprising", and "including" will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment. The term "about" in relation to a numerical value is optional and means, for example, +/−10%.

The words "preferred" and "preferably" are used herein refer to embodiments of the invention that may provide certain benefits under some circumstances. It is to be appreciated, however, that other embodiments may also be preferred under the same or different circumstances. The recitation of one or more preferred embodiments therefore does not mean or imply that other embodiments are not useful, and is not intended to exclude other embodiments from the scope of the disclosure, or from the scope of the claims.

Examples

Method 1—In-Line Crystallinity Detection of Piroxicam in Kollidon VA64

A twin-screw extruder was used to assess the solubility maximum for a mixture of the non-steroidal anti-inflammatory drug (NSAID) piroxicam (PRX) and the carrier polymer Kollidon VA64. The mixture was continuously analysed while traversing the extruder screw using a system of in-line UV/vis spectrometers and the input of the PRX was adjusted until crystallinity was first detected.

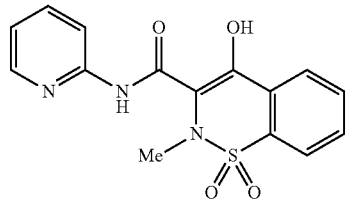 [SMILES: CN1C(C(=O)Nc2ccccn2)=C(O)c2ccccc2S1(=O)=O]

Formula 1. 4-hydroxy-2-methyl-1,1-dioxo-N-pyridin-2-yl-1$1^{6}$,2-benzothiazine-3-carboxamide (PRX)

Figure 2:
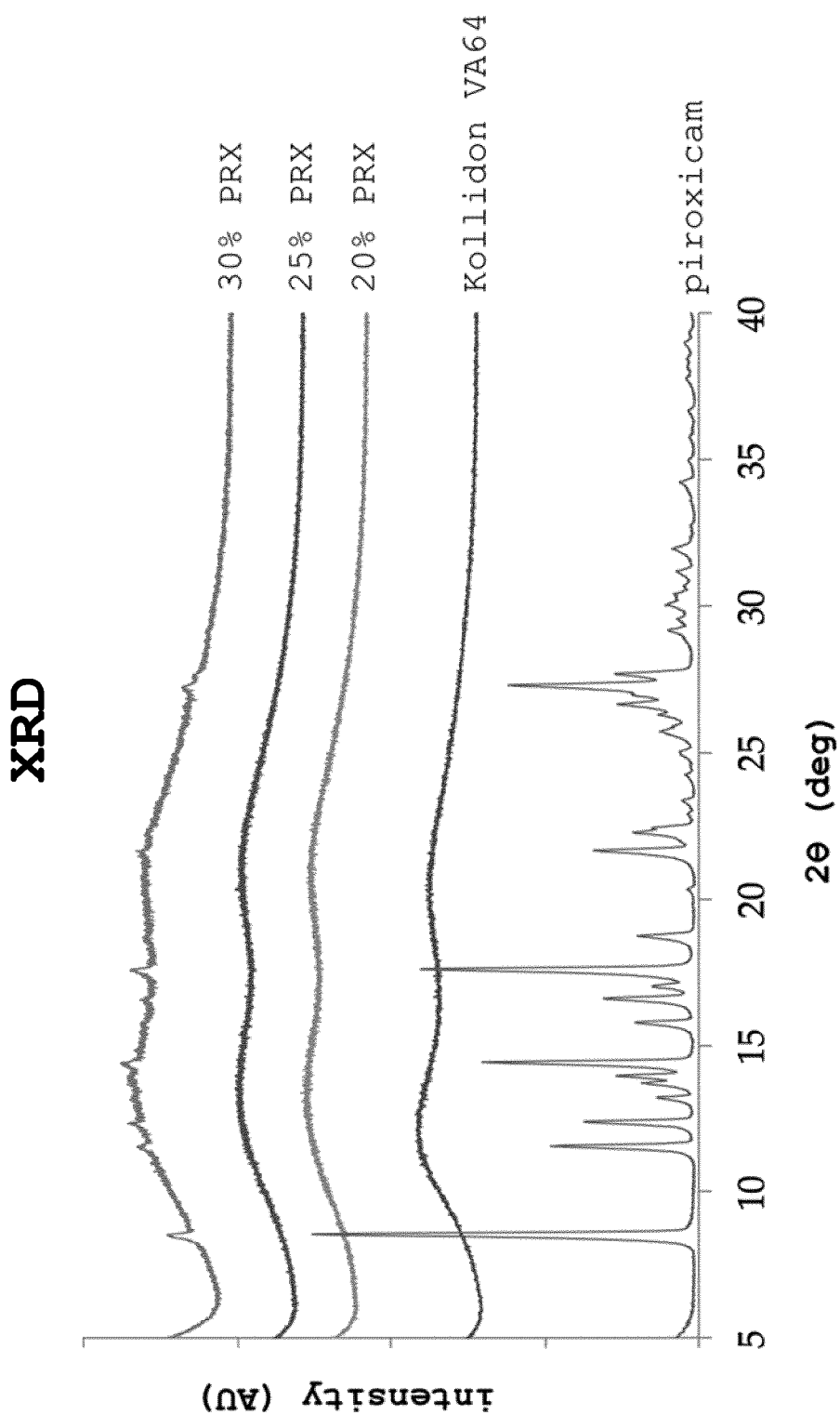
FIG. 2 shows five XRD spectra obtained on a Bruker instrument of pure solid PRX, Kollidon VA64, and 20, 25 and 30 wt % PRX mixtures. Traces of the XRD fingerprint of crystalline PRX are first observed in the 30% PRX spectra.

The samples were analysed by a UV/vis spectrometer in transmission mode (FIG. 1) and an XRD spectrum of the same samples was also obtained for comparison and verification (FIG. 2). The XRD samples required milling and analysis offline whereas UV/vis has the advantages that it can be performed rapidly in-line without milling.

UV/vis transmission spectra were obtained for 15, 18, 20, 23 and 25 wt % PRX samples. There is a clear overall absorbance increase between the 23 and 25 wt % PRX samples. This correlates with the observation that mixtures appear amorphous, homogeneous and transparent below 25 wt % PRX loading. However, at 25 wt % PRX, the first microcrystalline domains are observed, leading to increased scattering and a decrease in transmitted light (i.e. an increase in absorbance).

XRD spectra were obtained on a Bruker instrument for each of pure solid PRX, Kollidon VA64, and 20, 25 and 30 wt % PRX mixtures separately. By comparison, XRD does not detect the presence of crystallinity in the 25 wt % PRX mixture. Only at 30 wt % PRX loading, well above the maximum solubility when there is substantially higher crystallinity, does the XRD spectra first show peaks that correlate with the pure XRD spectra of PRX. The Kollidon VA64 spectra shows that the polymer component of the mixture is amorphous.

This experiment demonstrates that UV/vis can have a greater sensitivity to low amounts of crystallinity compared to XRD.

Method 2—UV/Vis Calibration Using a Milled Crystalline ETR Dilution Series

Etravirine (0.82271 g), sodium stearoyl fumarate (0.03291 g) and HMPC-E5 (2.444 g) were added to a small sealable plastic bag to provide a 25 wt % ETR mixture. The ETR was 100% crystalline. The HMPC-E5 was cryomilled for 20 minutes and dried before use.

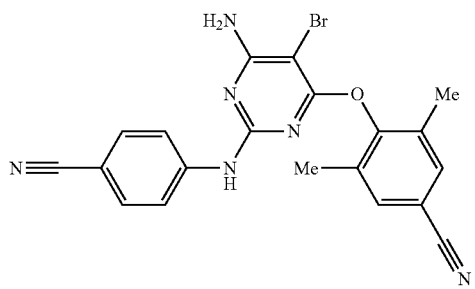 [SMILES: Cc1cc(C#N)cc(C)c1Oc1nc(Nc2ccc(C#N)cc2)nc(N)c1Br]

Formula 2. 4-[6-amino-5-bromo-2-(4-cyanoanilino)pyrimidin-4-yl]oxy-3,5-dimethylbenzonitrile (ETR)

The particle size distributions of the components were measured using a Mastersizer and are shown in the table below.

TABLE 1

Particle size distributions of the components.

| Component | D10 | D50 | D90 |
|---|---|---|---|
| crystalline etravirine (ETR) | 8 μm | 26 μm | 87 μm |
| HPMC-E5 (cryomilled for 20 minutes) | 3 μm | 17 μm | 60 μm |

The sealed bag was alternatively kneaded and shaken for 2 minutes in total. The resulting powder was used in a serial dilution series to provide mixtures having 20, 10, 5, 2.5, 1.25, 0.625 and 0.3125 wt % crystalline ETR. The diluent was a completely amorphous solid dispersion having the same ratios of ETF, SSF and HPMC-E5 to maintain the ETR loading at 25%.

Figure 3:
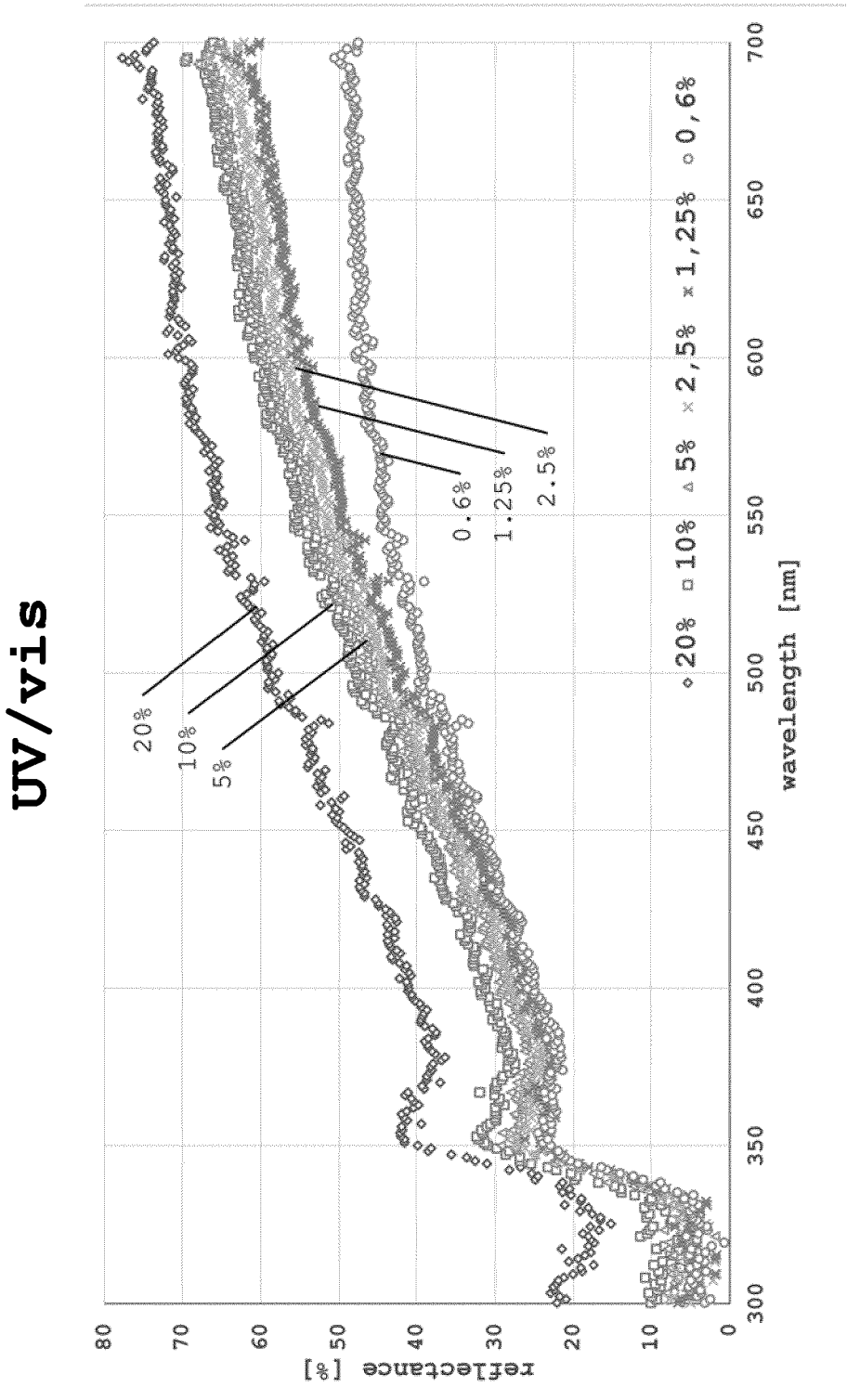
FIG. 3 shows overlaid UV/vis spectra for polymeric mixtures of HMPC-E5 (VIVAPHARM® hydroxypropyl methylcellulose) and sodium stearoyl fumarate (SSF) having 20, 10, 5, 2.5, 1.25 and 0.625 wt % crystalline etravirine.

Multiple UV/vis reflectance spectra were obtained for each sample of the serial dilution. A spectra for mixtures having 20, 10, 5, 2.5, 1.25 and 0.625 wt % crystalline ETR is shown in FIG. 3.

The overall reflectance increases with crystallinity at all measured wavelengths. There is a clear correlation between the amount of crystalline ETR (20 to 0.6 wt %) and the reflectance observed in each UV/vis spectrum. The amount of crystalline ETR was independently verified for the same samples using off-line XRD and Raman spectroscopy.

Figure 4:
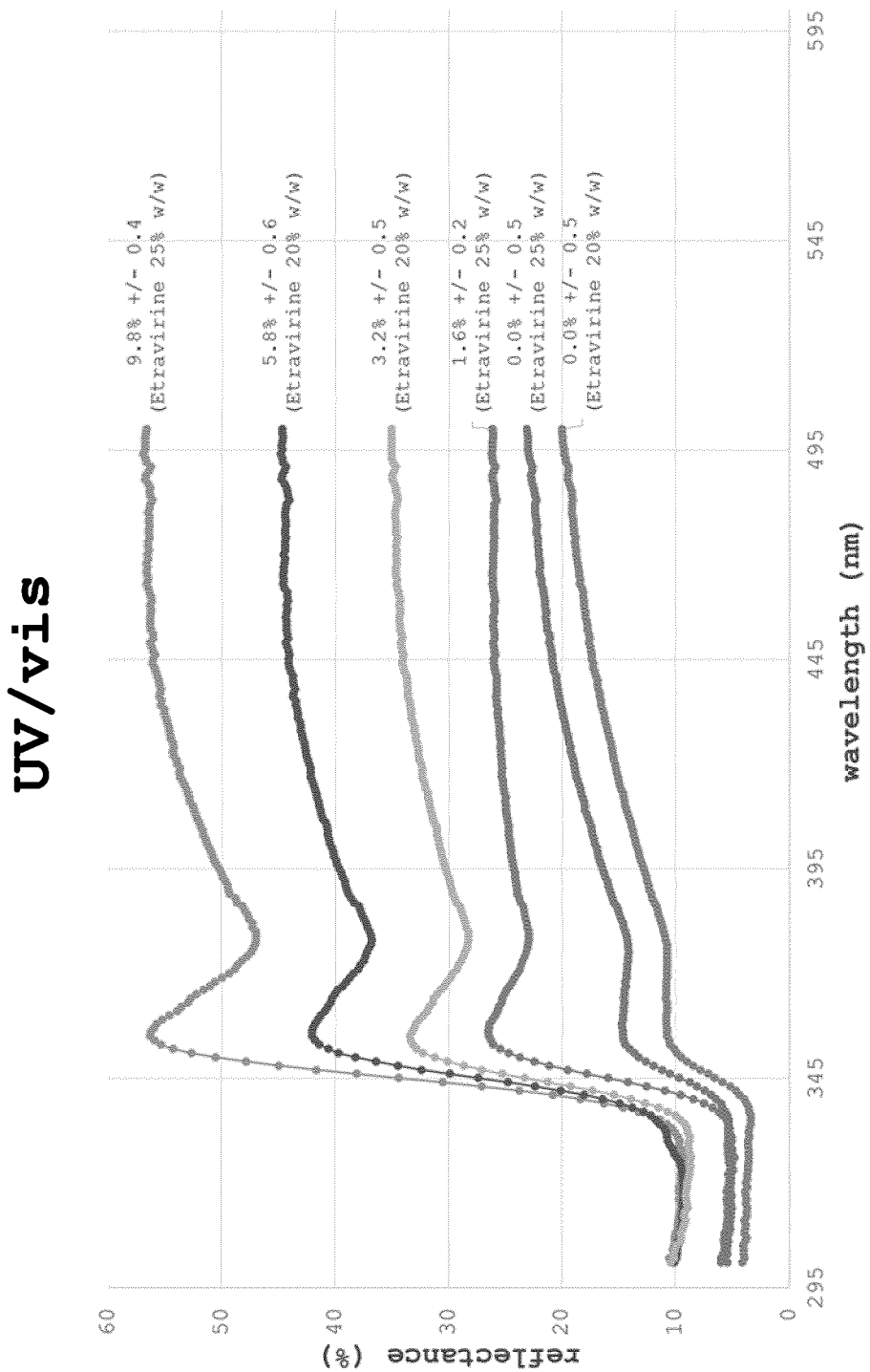
FIG. 4 shows overlaid UV/vis reflectance spectra for ETR dispersed in hydroxypropyl methyl cellulose (HMPC-E5) wherein the total amount of ETR is 20 or 25 wt %.

Furthermore, FIG. 4 shows overlaid UV/vis spectra of another series of ETR preparations that differ in crystallinity. The same clear correlation between the amount of crystalline ETR (0 to 9.8 wt %) and the reflectance observed in each UV/vis spectrum.

Method 3—Predictive Modelling of Crystallinity

Figure 9:
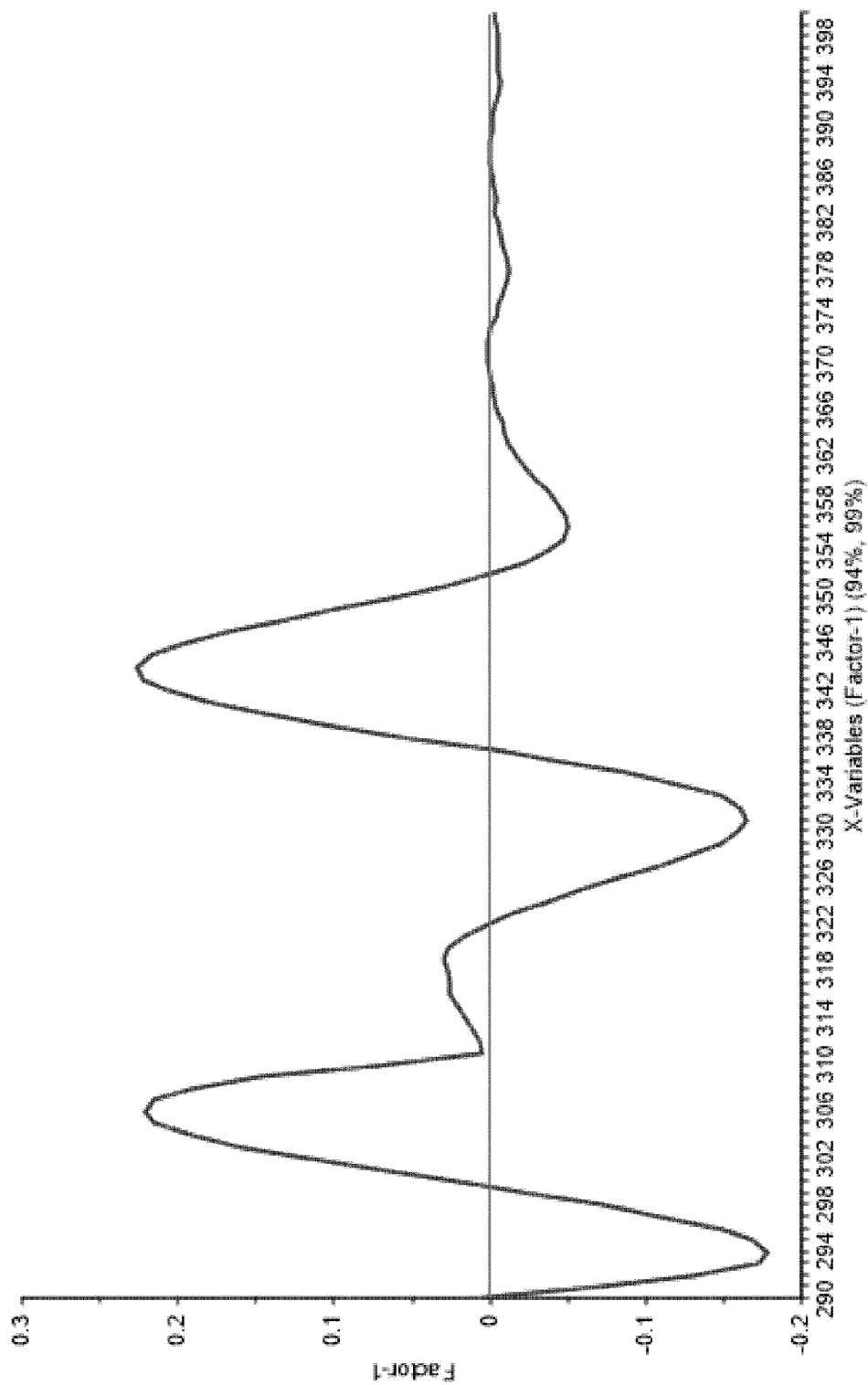
FIG. 9 shows a plot of loading contributing to Factor-1 (y-axis), the first principle component following PCA on the reflectance spectra ETR-containing samples as described in Method 3, against wavelength in nm from 290 to 400 (x-axis). As shown, Factor-1 provides the first eigenvector that explains the variance in the dataset.

To prepare a predictive model to determine crystallinity, each reflectance spectra for each amount of crystalline ETR in Method 2 was first converted to its second derivative and then processed by standard normal variate (SNV) analysis, and Savitzky Golay analysis was performed to generate a moving average across all data points in each spectrum. Following these data processing steps, which normalise and smooth the spectral data, the data were subjected to principle component analysis (PCA) to provide a first principle component (Factor-1) that was found to explain around 98% of the variance of the spectra (see FIGS. 9 and 10). The plot of Factor-1 (y-axis) against wavelength in the range 290-400 nm (x-axis) is shown in FIG. 9 and represents a simplified "spectrum" that best fits the whole dataset of the samples across the examined range of crystallinity.

Figure 10:
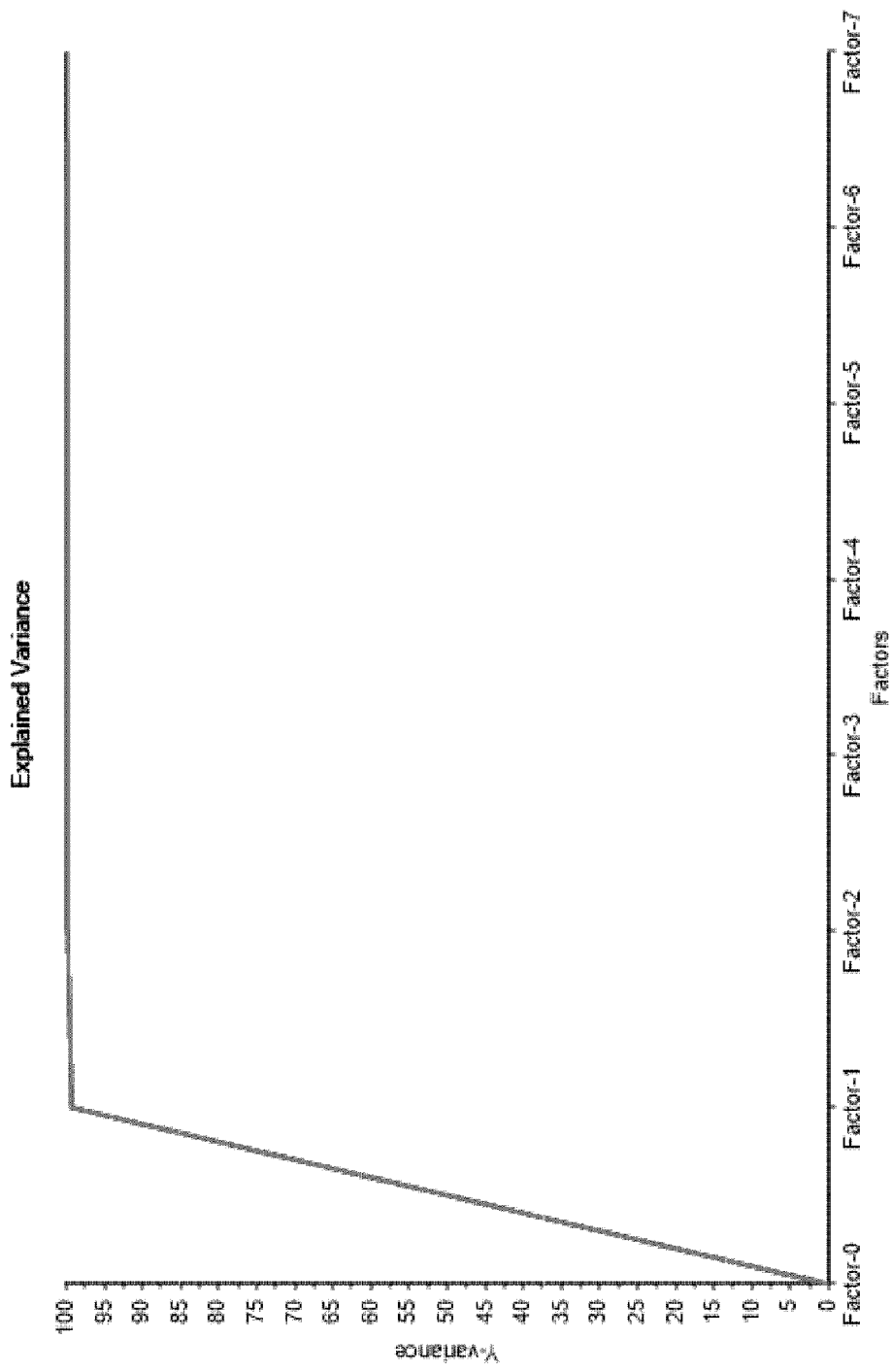
FIG. 10 shows a plot of variance (y-axis) against Factors in the PCA (x-axis), showing that Factor-1 and Factor-2 explain around 98% and 2% of the variance of the dataset, respectively.
Figure 11:
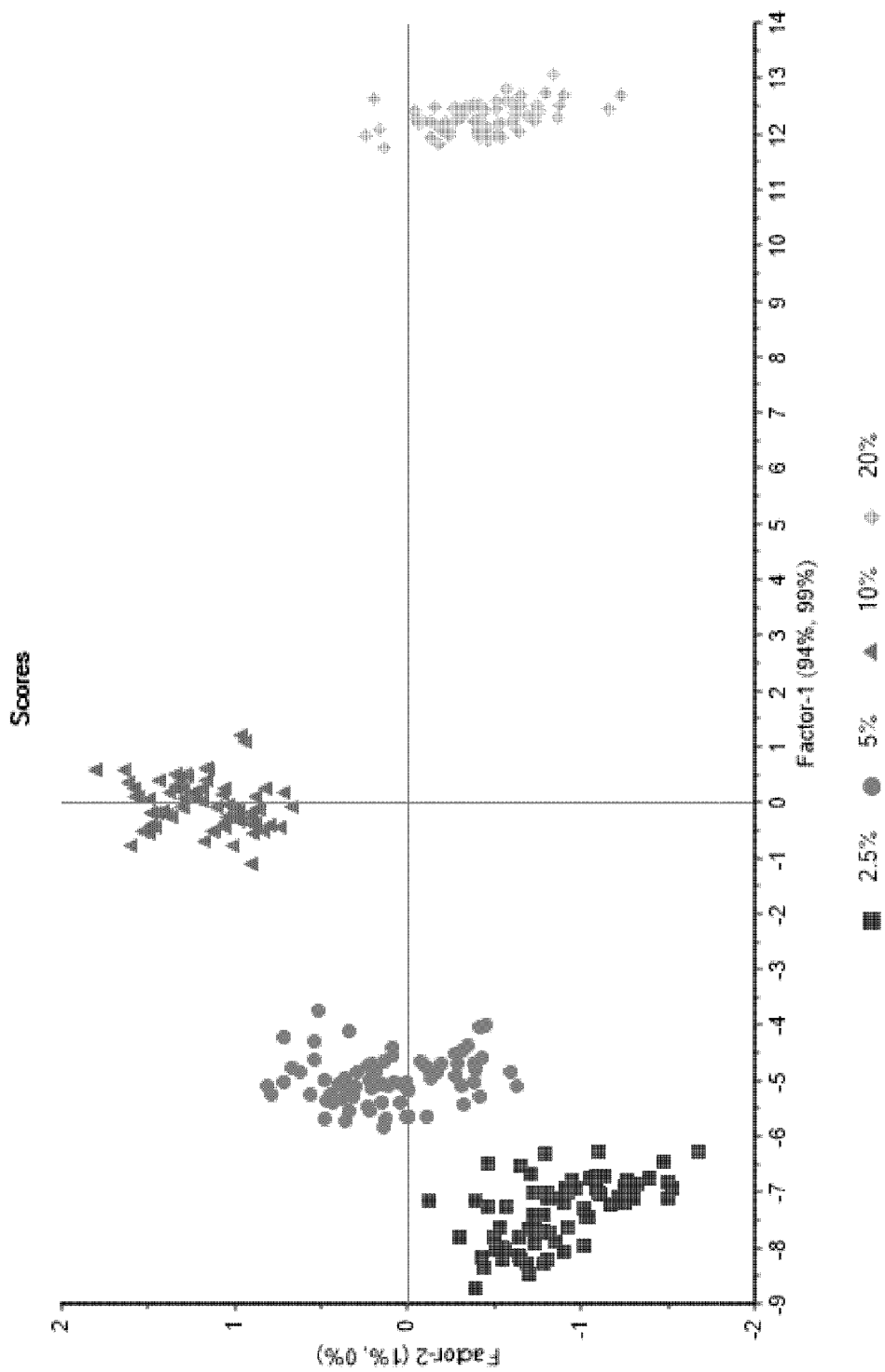
FIG. 11 shows a scatter plot of Factor-2 (y-axis) against Factor-1 (x-axis) derived from the PCA analysis in method 3. As can be seen the samples cluster according to crystallinity (i.e. 2.5% crystallinity samples (squares), 5% crystallinity samples (circles), 10% crystallinity samples (triangles) and 20% crystallinity samples (diamonds)).

Factor-2 largely explains the remaining 2% variation in the dataset (FIG. 10). A scatter plot of Factor-2 (y-axis) against Factor-1 (x-axis) is shown in FIG. 11. The samples were found to cluster according to crystallinity (i.e. 2.5% crystallinity samples (squares), 5% crystallinity samples (circles), 10% crystallinity samples (triangles) and 20% crystallinity samples (diamonds)). This shows that processing the UV/vis spectra data to form a PCA model successfully resolves the spectra, distinguishing the samples by crystallinity in the range 2.5-20%.

Figure 12:
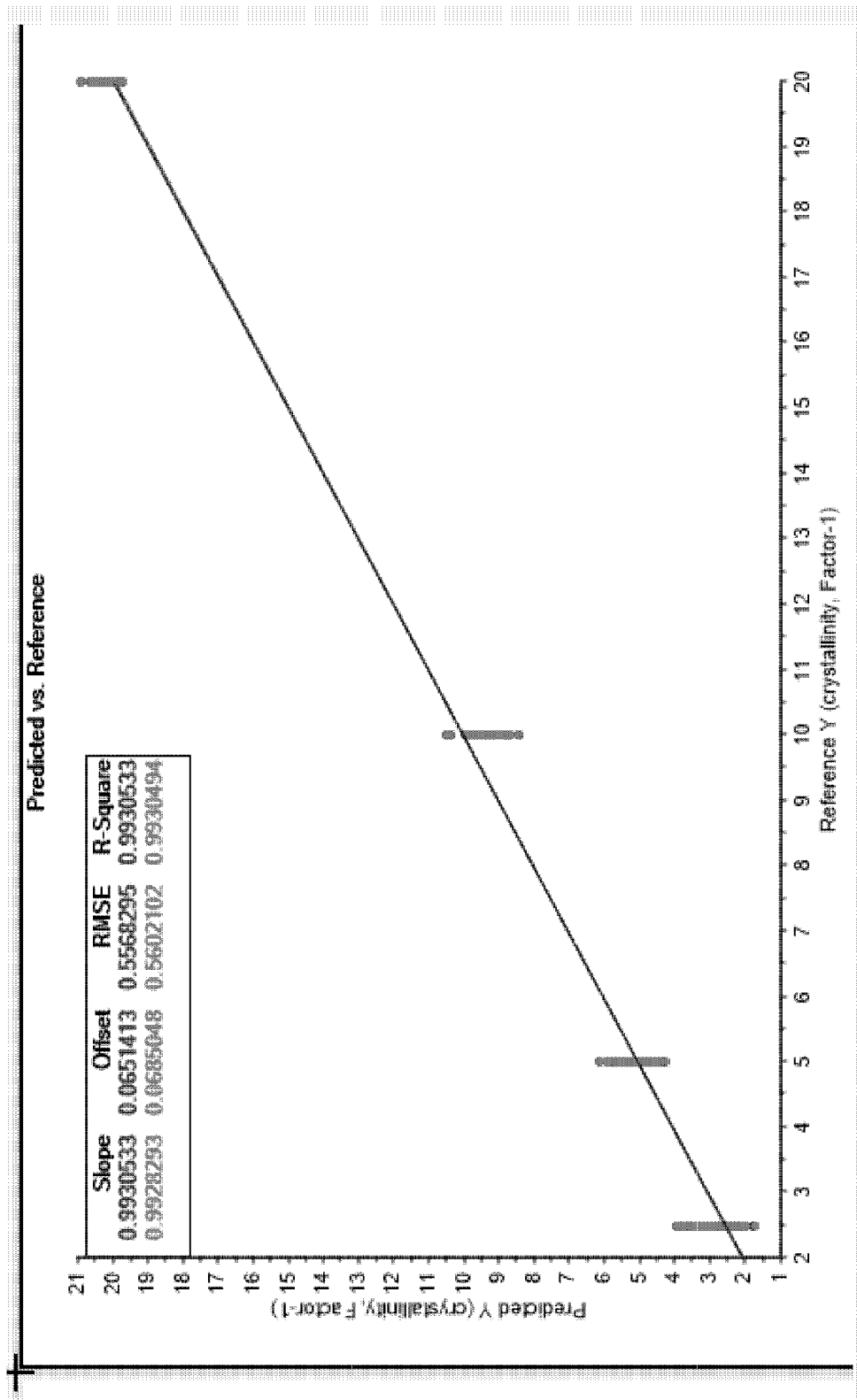
FIG. 12 shows a plot of the predicted crystallinity by Factor-1 (y-axis) against the known (reference) levels of crystallinity of the samples (x-axis). The inset shows the linearity of the correlation.

In FIG. 12, the predicted crystallinity by Factor-1 (y-axis) is plotted against the known (reference) levels of crystallinity of the samples (x-axis). A high degree of correlation is seen (R-squared values above 0.99). This example shows that processing the UV/vis spectra, optionally after data normalisation and/or smoothing, to generate a PCA model facilitates determination of crystallinity of one or more samples via the methods of the present invention.

Importantly, without wishing to be bound by any particular theory, the present inventors believe that many other API/carrier combinations will be amenable to such PCA modelling because PCA is an adaptable analysis that can be used to reduce the complexity or dimensionality of the spectral data without the need to understand what causes a particular spectral shape or pattern.

In some cases, the data may be further processed by partial least squares regression (PLSR) to conveniently compare and predict the crystallinity of sample(s) based on their UV/vis spectra, particularly with reference to a "standard curve" formed of values obtained from a plurality of reference samples of known crystallinity and which have the same API and carrier as the subject sample(s).

Because total reflectance and total absorbance of a sample vary with crystallinity, another way to model the UV/vis spectral data is to generate and plot the L* values of reference samples having a known and differing crystallinity.

Figure 5:
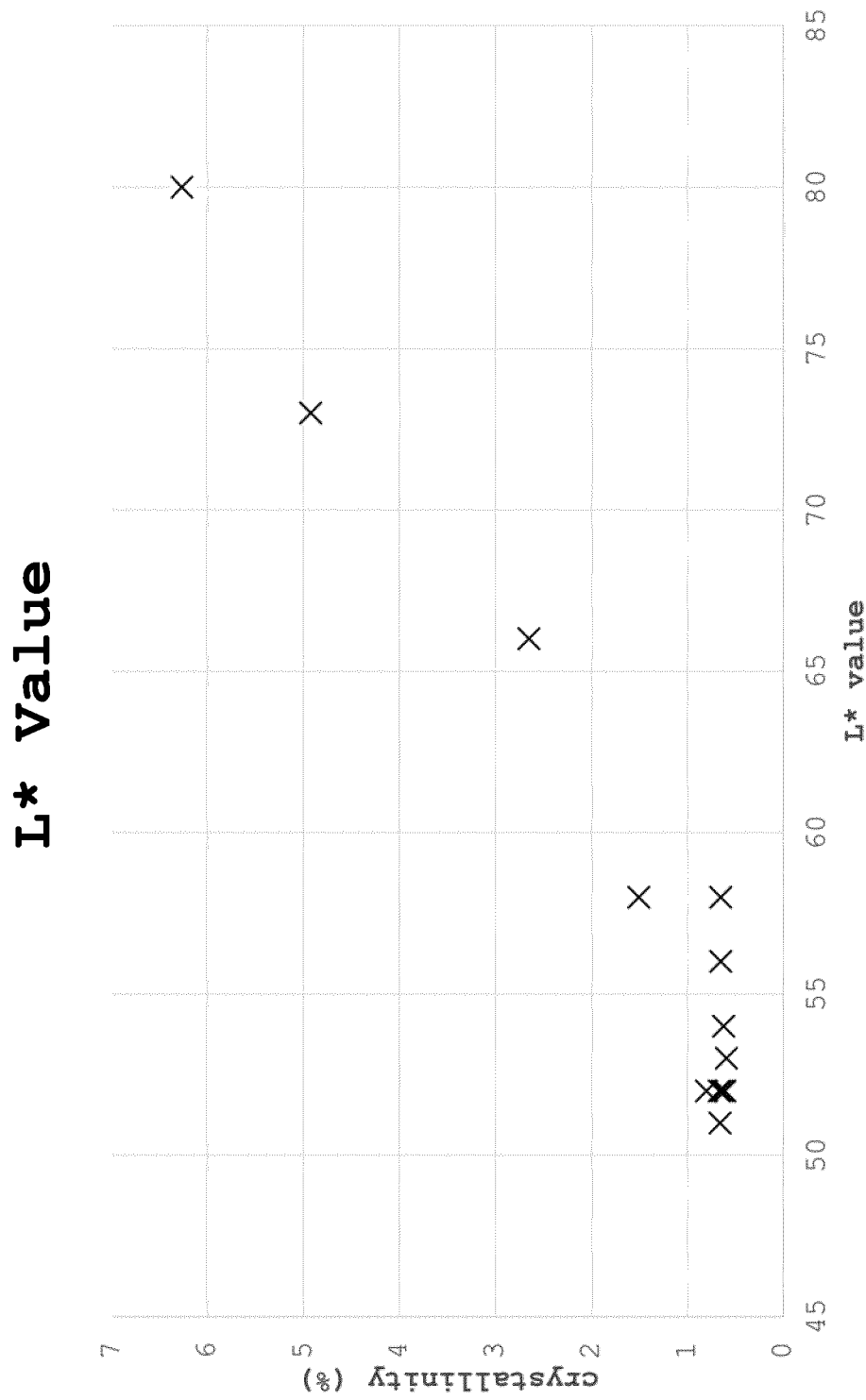
FIG. 5 shows a good correlation between L* value and crystallinity of thirteen unmilled ETR samples that each have different crystallinities as determined beforehand by Raman spectroscopy obtained on a Kaiser instrument. The total amount of ETR in each sample, including both amorphous and crystalline content, was 25 wt %. An unmilled sample is the direct solid monolithic form that results upon solidification after extrusion.
Figure 6:
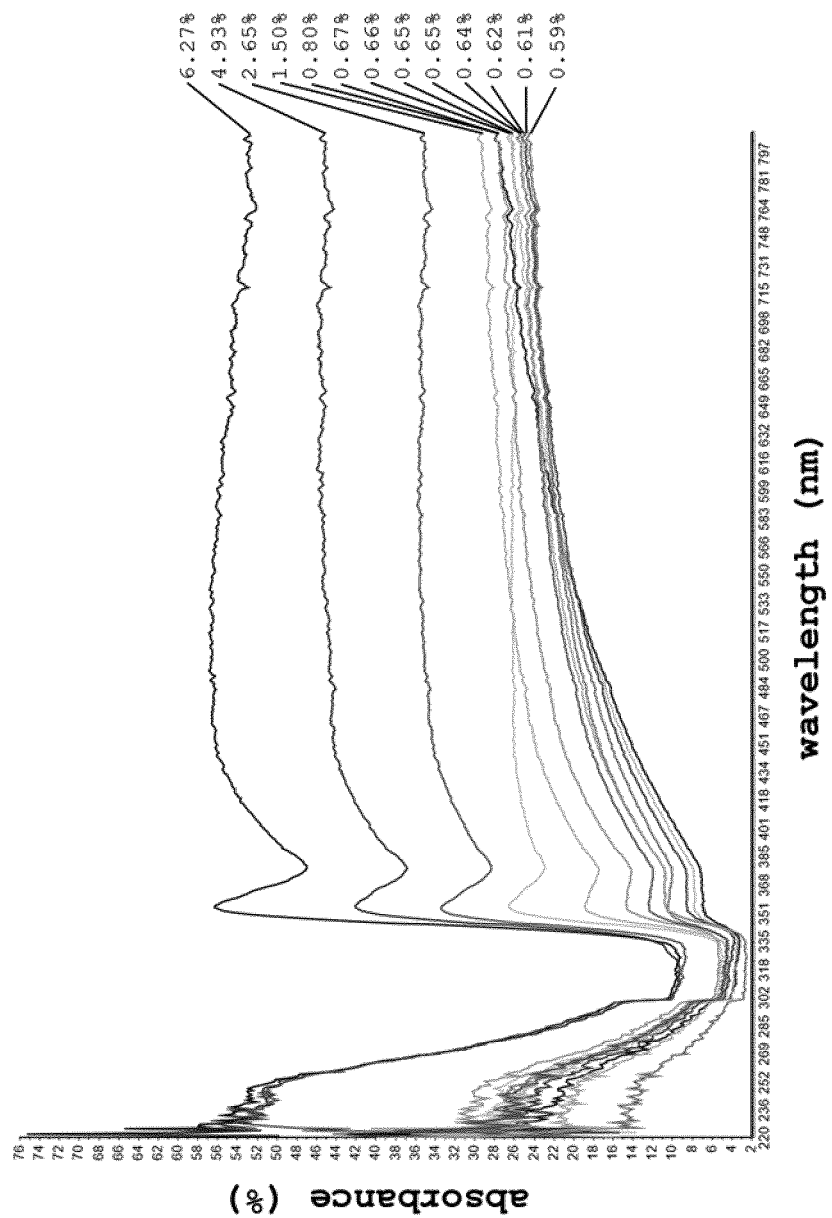
FIG. 6 shows the reflectance UV/vis transmission spectra at 220 to 800 nm for the same thirteen samples of ETR as FIG. 5.
Figure 7:
FIG. 7 shows the XRD spectra obtained on a Rigaku instrument for the same thirteen samples of ETR as FIG. 5.
Figure 8:
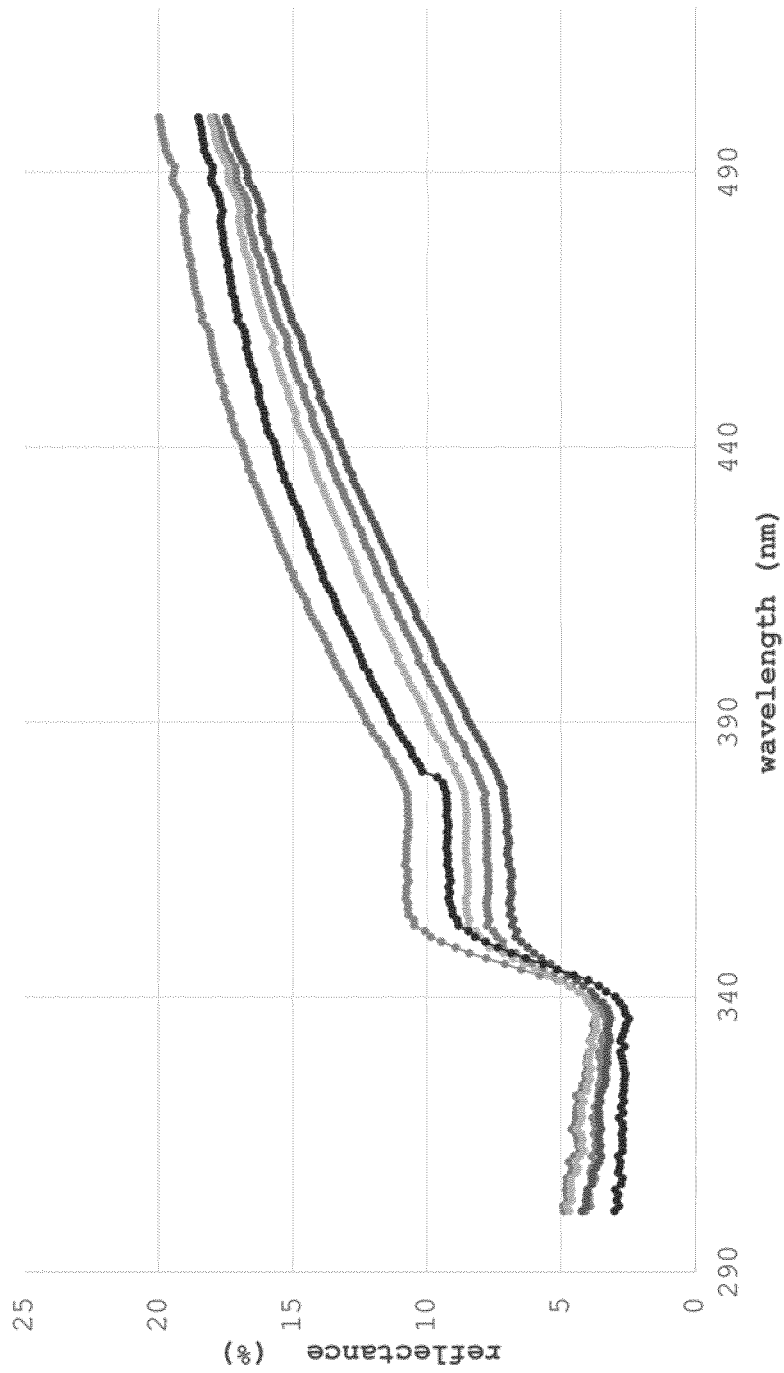
FIG. 8 shows the UV reflectance spectra for five of the thirteen ETR samples of FIG. 5 that have substantially no crystallinity (<1% as determined by Raman spectroscopy). Good reliability and reproducibility of the overall spectrum shape and reflectance amount between these very similar samples is observed.

L* is the lightness value component of L*a*b* according to 'CIELAB colour space' as defined by the International Commission on Illumination (CIE) where the darkest black is L*=0 and the brightest white is L*=100. Such a plot of L* value against crystallinity is shown in FIG. 5. A clear and linear correlation between crystallinity and L* value, particularly above 1% crystallinity, is observed.

The invention claimed is:

1. A method of generating a predictive model for determining an amount of crystallinity of an active pharmaceutical ingredient (API) in an amorphous solid dispersion or solid-state solution, the method comprising:
(i) subjecting a plurality of reference samples of dispersions or solutions spanning a range of API crystallinity to UV/vis spectroscopy using a UV/vis spectrometer;
(ii) measuring a reflectance and/or transmission spectrum of each reference sample using the UV/vis spectrometer wherein the reflectance and/or transmission is produced from subjecting the plurality of reference samples to UV/vis spectroscopy according to step (i); and
(iii) generating a predictive crystallinity model using principle component analysis (PCA) of the spectra from step (ii).

2. The method according to claim 1 wherein the plurality of reference samples comprises 5 or more reference samples and the spectra are pre-processed before step (iii) to normalize and/or smooth the spectra.

3. The method according to claim 2 wherein the spectra of the reference samples are processed to derive a feature that correlates with crystallinity across at least a portion of the range of crystallinity.

4. The method according to claim 3, wherein the feature comprises:
at least a first principal component derived from principal components analysis (PCA) of the spectra; or
a lightness value L* of CIELAB colour space derived from the spectra.

5. A method of testing a pharmaceutical composition comprising an active pharmaceutical ingredient (API) in an amorphous solid dispersion or solid-state solution for crystallinity of the API, the method comprising:
(i) subjecting the pharmaceutical composition comprising the API in the amorphous solid dispersion or solid-state solution to UV/vis spectroscopy using a UV/vis spectrometer;
(ii) measuring a reflectance and/or transmittance spectrum of the pharmaceutical composition comprising the API in the amorphous solid dispersion or solid-state solution using the UV/vis spectrometer wherein the reflectance and/or transmission is produced from subjecting the pharmaceutical composition to UV/vis spectroscopy according to step (i); and
(iii) determining the presence or absence of crystallinity of the API of the pharmaceutical composition by comparing a measured reflectance and/or transmittance spectrum obtained from step (ii) to a reflectance and/or transmittance spectrum for a completely amorphous sample.

6. The method according to claim 5, further comprising:
(iv) when crystalline API is found to be present, determining the amount crystallinity of the API in the amorphous solid dispersion or solid-state solution by comparing the measured spectrum to a predictive model for determining the amount of crystallinity of an API in the amorphous solid dispersion or solid-state solution, the predictive model being produced by
(i) subjecting a plurality of reference samples of dispersions or solutions spanning a range of API crystallinity to UV/vis spectroscopy using a UV/vis spectrometer;
(ii) measuring a reflectance and/or transmission spectrum of each reference sample using the UV/vis spectrometer wherein the reflectance and/or transmission is produced from subjecting the plurality of reference samples to UV/vis spectroscopy according to step (i); and
(iii) generating a predictive crystallinity model using principle component analysis (PCA) of the spectra from step (ii).

7. The method according to claim 5, wherein the amount of crystallinity in the amorphous solid dispersion or solid-state solution is measured at 1 wt % and above and at 50 wt % and below.

8. A method of manufacturing a pharmaceutical composition, comprising:
(i) forming an active pharmaceutical ingredient (API) into an amorphous solid dispersion or solid state solution that comprises the API;
(ii) testing the amorphous solid dispersion or solid-state solution for crystallinity of the API one or more times by
(a) subjecting the amorphous solid dispersion or solid-state solution comprising the API to UV/vis spectroscopy using a UV/vis spectrometer;
(b) measuring a reflectance and/or transmittance spectrum of the amorphous solid dispersion or solid-state solution comprising the API using the UV/vis spectrometer wherein the reflectance and/or transmission is produced from subjecting the amorphous solid dispersion or solid-state solution comprising the API to UV/vis spectroscopy according to step (a); and
(c) determining the presence or absence of crystallinity of the API in the amorphous solid dispersion or solid-state solution by comparing a measured reflectance and/or transmittance spectrum obtained from step (b) to a reflectance and/or transmittance spectrum for a completely amorphous sample; and
(iii) where the amorphous solid dispersion or solid-state solution has an amount of crystallinity within an acceptable range, processing the composition into a finished pharmaceutical product.

9. The method according to claim 8 wherein:
the forming of the API into the amorphous solid dispersion or solid-state solution is performed by extrusion, ball-milling, or spray drying; and/or
the testing of the amorphous solid dispersion or solid-state solution for the crystallinity of the API one or more times is performed in-line.

10. The method according to claim 9 wherein:
(a) the forming is performed by extrusion and the testing is performed at one or more of (i) the point of API input, (ii) upstream of the point of extrusion, or (iii) at the point of extrusion;
(b) the forming is performed by ball-milling in a ball mill having one or more transparent points wherein the testing is performed through the one or more transparent points substantially perpendicular to an axis of motion; or
(c) the forming is performed by spray drying and the testing is performed at one or more of (i) the point of API input, (ii) at the point of atomization in a drying chamber, or (iii) at the point of settling after atomization.

11. The method according to claim 10 wherein the acceptable range for crystallinity is 1 wt % or less and (i) the amount of API input to, (ii) the speed of, and/or (iii) the temperature of the screw extruder, ball mill, or spray drier is automatically adjusted, when required, to ensure crystallinity is within the acceptable range.

12. The method according to claim 11 wherein UV/vis reflectance and/or transmittance are measured continuously at wavelengths of 210 to 800 nm.

13. The method according to claim 12, wherein a particle size of the amorphous solid dispersion or solid-state solution is measured prior to being subjected to UV/vis spectroscopy; and the amorphous solid dispersion or solid-state solution is sized to match the size of one or more reference samples of known crystallinity, wherein the reference samples match the API and a carrier of the amorphous solid dispersion or solid-state solution.

14. The method according to claim 13, wherein the API is a compound of 2000 g/mol or less molecular weight, comprises 5 wt % or less water, and is at least 95% pure prior to being incorporated into the amorphous solid dispersion or solid-state solution.

15. The method according to claim 14, wherein the API is a non-nucleoside reverse transcriptase inhibitor (NNRTI) or a non-steroidal anti-inflammatory drug (NSAID).

16. The method according to claim 15, wherein the carrier of the amorphous solid dispersion or solid-state solution comprises an amorphous polymer and comprises 5 wt % or less water.

\* \* \* \* \*